United States Patent
Arbogast et al.

(10) Patent No.: US 7,846,386 B2
(45) Date of Patent: Dec. 7, 2010

(54) ANALYTE METER PROTECTORS AND METHODS

(75) Inventors: Frederic Arbogast, San Ramon, CA (US); Paul Strasma, Oakland, CA (US); Lawrence Azzano, Seattle, WA (US); Kenneth Gary, Boxborough, MA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

(21) Appl. No.: 12/495,642

(22) Filed: Jun. 30, 2009

(65) Prior Publication Data

US 2009/0270697 A1 Oct. 29, 2009

Related U.S. Application Data

(63) Continuation of application No. 11/960,156, filed on Dec. 19, 2007.

(60) Provisional application No. 60/871,910, filed on Dec. 26, 2006.

(51) Int. Cl.
*G01N 15/06* (2006.01)

(52) U.S. Cl. .................... 422/68.1; 422/55; 422/58; 422/61; 422/82.05; 422/103; 422/104

(58) Field of Classification Search .................. 422/55, 422/58, 61, 68.1, 82.05, 103, 104
See application file for complete search history.

(56) References Cited

U.S. PATENT DOCUMENTS

| | | | |
|---|---|---|---|
| 4,545,382 A | 10/1985 | Higgins et al. | |
| 4,711,245 A | 12/1987 | Higgins et al. | |
| 4,774,192 A | 9/1988 | Terminiello et al. | |
| 5,232,668 A * | 8/1993 | Grant et al. | 422/82.05 |
| 5,279,294 A | 1/1994 | Anderson et al. | |
| 5,509,410 A | 4/1996 | Hill et al. | |
| 5,526,120 A | 6/1996 | Jina et al. | |
| 5,593,390 A | 1/1997 | Castellano et al. | |
| 5,628,890 A | 5/1997 | Carter et al. | |
| 5,820,551 A | 10/1998 | Hill et al. | |
| 6,071,391 A | 6/2000 | Gotoh et al. | |
| 6,120,676 A | 9/2000 | Heller et al. | |
| 6,143,164 A | 11/2000 | Heller et al. | |
| 6,175,752 B1 * | 1/2001 | Say et al. | 600/345 |
| 6,183,274 B1 | 2/2001 | Allum | |
| 6,268,162 B1 | 7/2001 | Phillips et al. | |
| 6,299,757 B1 | 10/2001 | Feldman et al. | |
| 6,338,790 B1 | 1/2002 | Feldman et al. | |
| 6,377,894 B1 | 4/2002 | Deweese et al. | |
| 6,461,496 B1 | 10/2002 | Feldman et al. | |
| 6,503,381 B1 | 1/2003 | Gotoh et al. | |
| 6,506,168 B1 | 1/2003 | Fathallah et al. | |

(Continued)

FOREIGN PATENT DOCUMENTS

EP          1112717 A1       7/2001

(Continued)

*Primary Examiner*—Lyle A Alexander
*Assistant Examiner*—Dennis M White
(74) *Attorney, Agent, or Firm*—Edward J. Baba; Peter A. Socarras; Bozicevic, Field & Francis LLP

(57) ABSTRACT

Analyte meter protectors, meters that include the same, and methods.

17 Claims, 5 Drawing Sheets

U.S. PATENT DOCUMENTS

| | | |
|---|---|---|
| 6,514,460 B1 | 2/2003 | Fendrock |
| 6,514,718 B2 | 2/2003 | Heller et al. |
| 6,540,891 B1 | 4/2003 | Stewart et al. |
| 6,591,125 B1 | 7/2003 | Buse et al. |
| 6,592,745 B1 | 7/2003 | Feldman et al. |
| 6,600,997 B2 | 7/2003 | Deweese et al. |
| 6,616,819 B1 | 9/2003 | Liamos et al. |
| 6,618,934 B1 | 9/2003 | Feldman et al. |
| 6,676,816 B2 | 1/2004 | Mao et al. |
| 6,730,200 B1 | 5/2004 | Stewart et al. |
| 6,736,957 B1 | 5/2004 | Forrow et al. |
| 6,749,740 B2 | 6/2004 | Liamos et al. |
| 6,764,581 B1 | 7/2004 | Forrow et al. |
| 6,773,671 B1 | 8/2004 | Lewis et al. |
| 6,850,283 B1 | 2/2005 | Tatamiya |
| 6,893,545 B2 | 5/2005 | Gotoh et al. |
| 6,942,518 B2 | 9/2005 | Liamos et al. |
| 2003/0191415 A1 | 10/2003 | Moerman et al. |
| 2004/0073095 A1 | 4/2004 | Causey et al. |
| 2004/0086425 A1 | 5/2004 | Jaunakais |
| 2004/0143173 A1* | 7/2004 | Reghabi et al. ............. 600/365 |
| 2004/0267300 A1 | 12/2004 | Mace |
| 2005/0121826 A1 | 6/2005 | Hajizadeh et al. |
| 2005/0125162 A1 | 6/2005 | Hajizadeh et al. |
| 2005/0154271 A1 | 7/2005 | Rasdal et al. |
| 2005/0281706 A1 | 12/2005 | Funke et al. |
| 2006/0040333 A1 | 2/2006 | Zocchi |
| 2006/0148096 A1 | 7/2006 | Jina |
| 2007/0100222 A1 | 5/2007 | Mastrototaro et al. |
| 2007/0247793 A1 | 10/2007 | Carnevali |
| 2008/0099332 A1 | 5/2008 | Scott et al. |
| 2008/0234559 A1 | 9/2008 | Arbogast et al. |

FOREIGN PATENT DOCUMENTS

| | | |
|---|---|---|
| EP | 1543935 A2 | 6/2005 |
| EP | 1712910 A1 | 10/2006 |
| WO | 2006/002432 | 1/2006 |

* cited by examiner

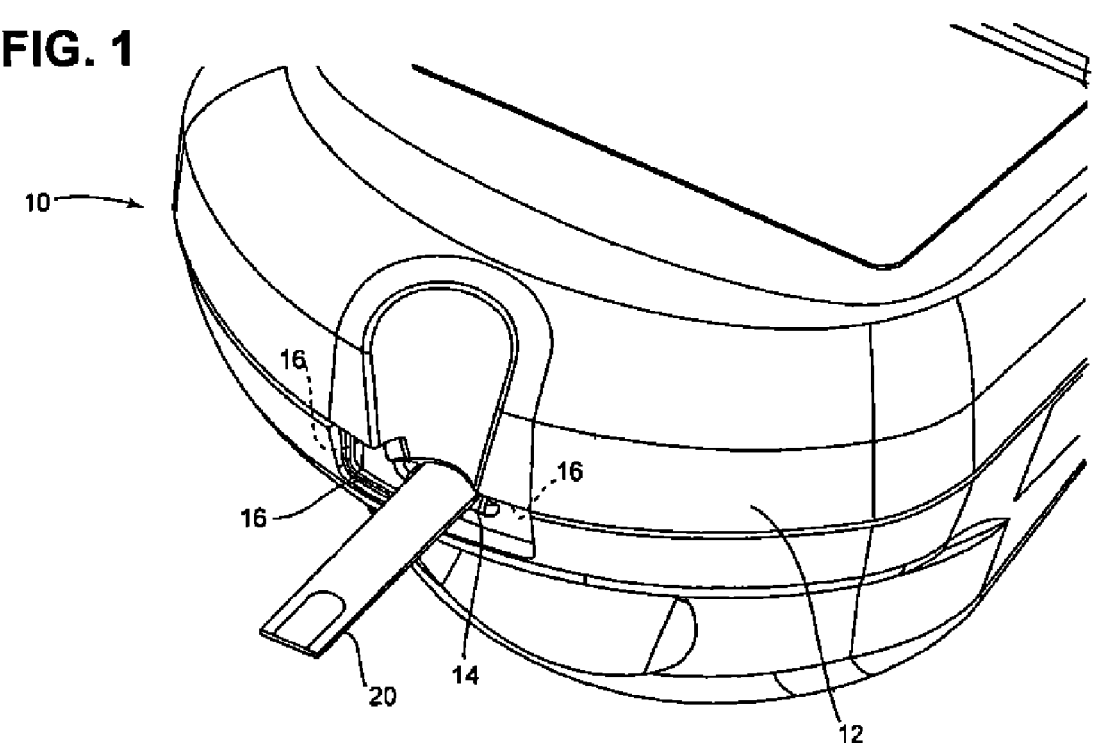

ANALYTE METER PROTECTORS AND METHODS

This application is a continuation of U.S. patent application Ser. No. 11/960,156, filed on Dec. 19, 2007; which application claims the benefit of priority to U.S. Provisional Application Ser. No. 60/871,910 that was filed with the United States Patent and Trademark Office on Dec. 26, 2006; both of which are hereby incorporated by reference.

BACKGROUND OF THE INVENTION

Analytical testers, also sometimes referred to as sensors, are commonly used to monitor the level of an analyte in a body fluid. For example, diabetics use analyte testers to monitor body glucose levels.

Analyte testing may involve testing once per day, but typically should be carried out periodically throughout the day using multiple analyte testers—one tester for each test. To "read" a tester, i.e., to analyze the body fluid applied to a tester and determine one or more analyte levels, a tester reader, oftentimes referred to as a "meter", is used. Either before or after a sample of body fluid is applied to a tester, the tester is received by the meter. The meter performs various functions and analyzes the tester-applied sample to provide an analyte level to the user.

The tester receiving area of a meter, commonly referred to as a tester "port", is the opening in a meter that receives a tester for testing. The tester port is therefore an opening from the outside meter environment to the interior of the meter. Because the interior is exposed to the outside environment via the tester port, the potential for contaminating materials to enter the meter's interior through the port exists. For example, unintended fluid ingress into the port from blood, interstitial fluid, control solution, cleaning fluid, or other fluids may occur. This unintended fluid ingress may interfere with the readings and confound the analyte results. Given the importance of obtaining accurate analyte level readings, it is imperative that the meter does not become contaminated.

Accordingly, as meters continue to be used for analyte monitoring, there continues to be an interest in analyte monitoring devices that are protected from contamination. Of interest are port protectors that are easily removable and replaceable, e.g., disposable.

SUMMARY OF THE INVENTION

Analyte testing medical devices, and components for use with the same, as well as methods of using the medical devices and components for analyte testing are provided.

Various embodiments include a meter port protector attachable to an area of a meter tester port. In many embodiments, a protector is disposable, e.g., easily removable and attachable.

In certain embodiments, a protector includes a slot for receiving an analyte tester. The slot may be dimensioned to provide minimal clearance between a surface of the slot and a surface of a received tester. For example, in certain embodiments a protector slot may be dimensioned to swipe or squeegee across a fluid-containing surface of a received tester. This may be useful to prevent unwanted fluid from entering the tester port of the meter and/or to meter the sample.

In many embodiments, the area defined by the opening of a protector is less than the area defined by the port of a meter. In this manner, the size of the opening to the meter is reduced by the protector.

Embodiments also include self aligning protectors. These protectors include features that correctly position the protectors with corresponding meters.

Also provided are analyte meters that include a tester port. Embodiments include meters having port protector removably secured about the ports. In certain embodiments, the protectors include a slot for receiving a tester.

Also included are methods, where embodiments include attaching, e.g., permanently or temporarily, a port protector about a port area of a meter. In certain embodiments, the methods include attaching a protector to a meter to reduce the size of the area defined by the meter port. Embodiments also include removing a first port protector from a meter and attaching a second protector to the meter. This may be particularly useful in hospital or analogous settings in which a single meter may be used to read a plurality of testers, at least some of which may be testing sample from different individuals.

Various methods may be employed to connect a protector to meter. Such methods include removable connecting a protector to a meter, e.g., using an adhesive, releasable tabs, etc.

Also provided are systems and kits that include an analyte meter and/or port protector and/or analyte tester, and/or lancing device. In certain embodiments, a plurality of protectors may be provided to a user, e.g., bundled together such as in a kit.

These and various other features which characterize the invention are pointed out with particularity in the attached claims. For a better understanding of the testers of the invention, their advantages, their use and objectives obtained by their use, reference may be made to the drawings and to the accompanying description, in which there is illustrated and described various embodiments of the invention.

BRIEF DESCRIPTION OF THE DRAWINGS

Referring now to the drawings, wherein like reference numerals and letters indicate corresponding structure throughout the several views:

FIG. 1 is an isometric front view of an exemplary embodiment of an analyte meter;

DETAILED DESCRIPTION

Figure 2A:
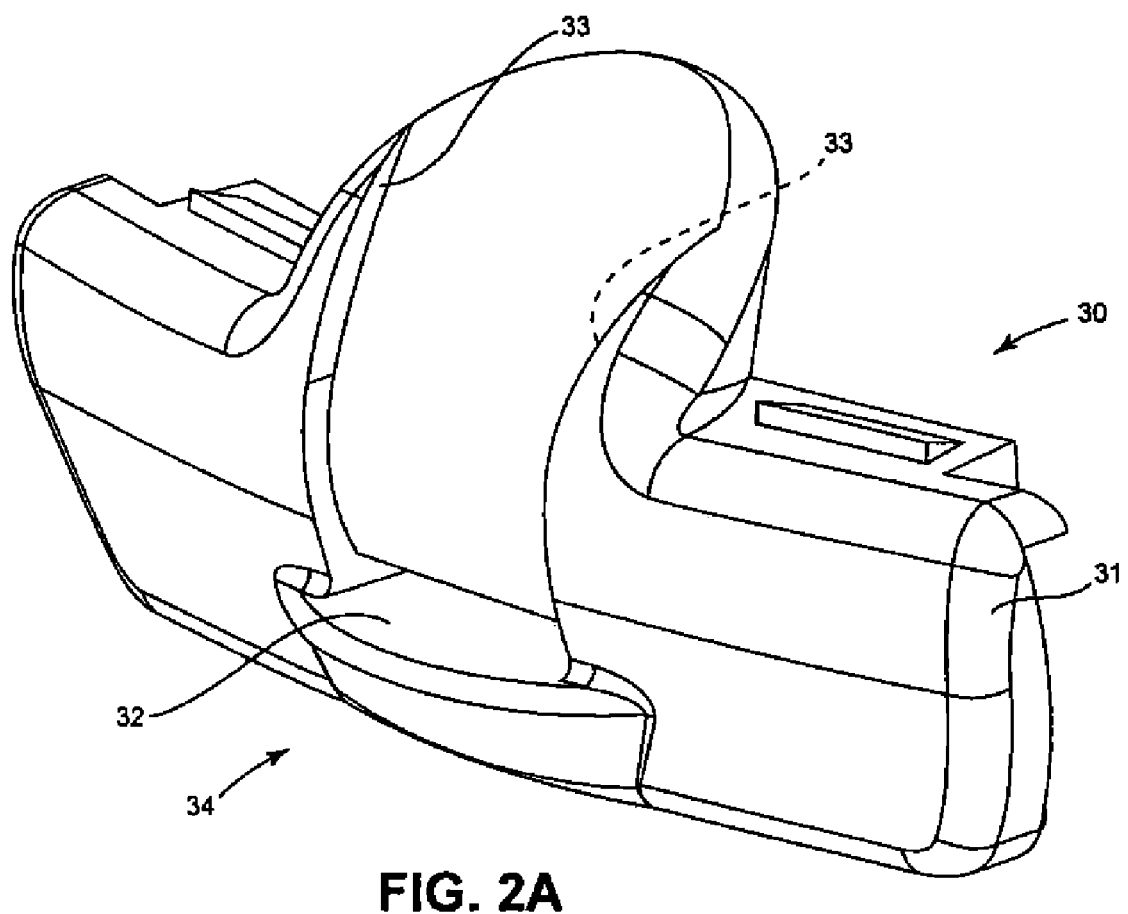
FIG. 2A is an isometric front view of an exemplary embodiment of a port protector.

As summarized above, protectors positionable about a tester opening or port of an analyte monitoring device are provided. The protectors are designed to mate with meters and more specifically mate with port areas. The protectors are particularly useful in preventing contaminants from entering the meters through the tester ports.

The protectors may be adapted to be used with any medical device having an opening and are particularly useful as adapted to be used with an analyte monitoring medical device having an opening for receiving a tester (also referred to as a test strip or sensor), such as an in vitro analyte monitoring meter or in vivo analyte monitoring system, e.g., those provided by Abbott Diabetes Care Inc. of Alameda, Calif.

Port-containing meters may be electrochemical or optical meters, and may be configured to determine the level of one or more analytes, where analytes include, but are not limited to, glucose, blood β-ketone, ketone bodies, lactate, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin, in sample of body fluid. Meters may also be configured to determined the concentration of drugs, such as, for example, antibiotics (e.g., gentamicin, vancomycin, and the like), digitoxin, digoxin, drugs of abuse, theophylline, and warfarin, may also be determined and the like, in a sample of body fluid. In certain embodiments, the protectors are shaped and sized to cooperate with a FreeStyle® brand blood glucose monitoring meter or a Precision® M brand blood monitoring meter capable of monitoring glucose and ketones, or other such analyte meters. The protectors may find use in meters designed for use in a hospital or similar clinic environment where a single meter may be used for a plurality of patients. Such systems include, but are not limited to, Precision PCx meters and FreeStyle Connect meters and Precision Xceed Pro manufactured by Abbott Diabetes Care.

In certain embodiments, the protectors may be configured to mate with a port of a continuous analyte monitoring system. For example, a continuous glucose monitoring system may include a component that receives analyte data from a transcutaneously positioned or wholly implanted inserted glucose sensor, and which component may be configured to communicate analyte results to the user, e.g., audibly by way of a display, or visually. The continuous monitoring system receiver may include a conventional blood glucose meter and therefore a port for accepting a glucose tester. For example, an analyte meter may be incorporated into a module of a continuous analyte monitoring system, e.g., a transmitter module, receiver module, etc. Such may be convenient for calibrating and/or confirming the continuous system. The conventional meter and test strip may be used to calibrate the continuous system (see for example U.S. Pat. No. 6,175,752), e.g., using one point calibration or other calibration protocol. It is to be understood that meters includes stand-alone meters, as well those operably connected to, e.g., integrated with) continuous analyte monitoring systems. Exemplary testers and meters and continuous analyte monitoring systems (sometimes referred to as in vivo system) include testers and meters such as those described, e.g., in U.S. Pat. Nos. 6,071, 391; 6,120,676; 6,143,164; 6,299,757; 6,338,790; 6,377,894; 6,600,997; 6,773,671; 6,514,460; 6,592,745; 5,628,890; 5,820,551; 6,736,957; 4,545,382; 4,711,245; 5,509,410; 6,540,891; 6,730,200; 6,764,581; 6,299,757; 6,338,790; 6,461,496; 6,503,381; 6,591,125; 6,616,819; 6,618,934; 6,676,816; 6,749,740; 6,893,545; 6,942,518; 6,175,752; and 6,514,718, and elsewhere. In certain embodiments, the port may be included in, e.g., integrated, a drug delivery system, e.g., in an insulin pump module such a pump or controller module thereof.

In certain embodiments, ports may include a tester slot. A slot is a passage through the body of the protector. Such a slot is dimensioned to admit an analyte tester. As such, certain embodiments include slots that are alignable with a meter port when the protector is connected to the meter. In this manner, when a protector is positioned about a meter port, a tester may be easily passed through the protector slot and into the port.

The slots may be any suitable dimension. In certain embodiments, a slot may be sized and shaped to provide minimal clearance between at least one surface of the slot and at lest one surface of a received tester. For example, clearance may be one the order of millimeters, e.g., less than about 2.5 mm, e.g., less than about 1 mm. In certain embodiments at least one surface of a protector slot may be configured to contact at least one surface of tester, e.g., to swipe or squeegee across a fluid-containing surface of a received tester. This may be useful to prevent unwanted fluid from entering the tester port of the meter and/or to meter the sample.

In many embodiments, the area defined by the opening of a protector is less than the area defined by the port of a meter. In this manner, the size of the opening to the meter is reduced by the protector. For example, in certain embodiments, the area defined by a slot of a protector may be less than 100% of the area defined by a port of a meter to which it is attachable, e.g., the area defined by a slot of a protector may be less than 100% of the area defined by a port of a meter, e.g., may be less than 80% of area defined by a port of a meter.

The slots may be any suitable shape. The shape may depend at least in part on the shape of the tester the meter is designed to accept. In certain embodiments, the slots may be substantially rectangular, e.g., in instances in which a substantially rectangular tester is employed. Other slot shapes may of course be used as well.

In certain embodiments, the slot may include a flexible valve that is disposed at least partially across the slot, and in some embodiments completely across the slot. The flexible valve may include self-sealing slit(s) which open to permit a tester therethrough in response to increased pressure on the slits, e.g., by a tester being pushed there against.

In many embodiments, the protectors do not apply pressure to a tester received in the slot of the protector.

Port protectors may be fixedly attached/attachable to a meter, or may be wholly removable from a meter. For example, a protector may be attachable to a meter over the port, but yet easily removable by a user when access to the tester port is desired and/or when replacement with another protector is desired. One or more engagement features may be used. An engagement feature(s) may be positioned on a protector and/or a meter. In certain embodiments adhesive is employed on a meter-contacting surface of a protector. The adhesive may be any suitable adhesive, such as contact adhesives, pressure sensitive adhesives, glues, epoxies, adhesive resins, and the like. In certain embodiments, the adhesive is applied to a membrane of suitable thickness, e.g. foam. The adhesive may be covered by a removable release liner to protect the adhesive from the environment until use. The release liner may be any convenient material, where representative release films include polyesters, such as PET or PP, and the like.

In certain embodiments molded features may be used. Such features may help to attach a protector to a meter and/or align a protector with the meter, e.g., particularly for embodiments that include a slot. Molded features may be used to align the protector slot with the port so that a tester may pass through the slot and into the port. For example, a rib(s) or tab(s) may be used. One or more ribs (on a protector and/or meter) may cooperate with a mating feature. Embodiments also include protectors configured to snap fit and/or friction fit with a meter. In certain embodiments, a meter-contacting surface of a protector may have a form that corresponds to a meter's surface, e.g., may be a negative of a meter surface. In certain embodiments, a portion of a protector may be fixedly attached to a meter, allowing the unattached portion to move away from the meter. This may be useful for cleaning the protector. In certain embodiments, the interface of a coupled meter and protector provides a substantially fluid tight seal.

In certain embodiments, a protector may also be configured to guide a tester into a port. For example, a protector having a slot may include guides, rails, channels, indentions, recessed structures, elevated structures, clamps, or the like, about the slot. Certain embodiments include a ledge. The ledge may be an extension of a slot, e.g., a bottom of a slot may include ledge. It will be appreciated that words such as "top", "bottom", "upper", and "lower", and the like, are used in a relative sense only. In certain embodiments, a protector may include spaced apart guides. With this or analogous configurations, a tester may be slid into position along the guides. The guides may be dimensioned such that a tester is snugly fit between the guides when it is mounted between the guides. During positioning of the tester, portions of the tester may be gripped (such as with a user's fingers) and the gripped portions used to then slide the tester into the mounted position between the guides.

The protectors may be made of any suitable material and may be substantially rigid or substantially flexible. In certain embodiments, the material is substantially flexible. Elastomeric materials may be used, e.g., rubber, or other compliant material. For example, foam may be used. In certain embodiments, the material may be a thermoplastic elastomer (TPE), thermoplastic urethane (TPU), polycarbonate (PC), acrylonitrile butadiene-styrene (ABS) or a combination of two or three of these. In certain embodiments, a protector has a hard plastic frame (e.g., PC-ABS) with a compliant area around the port opening.

Referring now to the Figures, FIG. 1 shows an isometric front view of an exemplary embodiment of an analyte meter 10. Meter 10 includes housing 12 defining an interior space and having a tester port 14 for receiving a tester. An exemplary analyte tester 20 is shown positioned in port 14 to be read by the meter. Analyte tester 20, e.g., a glucose tester, is shown as having a generally rectangular shape, but it is understood that any shaped tester may be used. Analyte tester 20 can be any tester suitable for use with meter 10. Examples of testers 20 are disclosed, for example, in U.S. Pat. Nos. 6,299,757, 6,591,125, and 6,616,819. The tester may have a sample chamber volume, for receive of sample (e.g., blood) to be tested, of no more than about 1 microliter, and in some embodiments, a volume of no more than about 0.5 microliter or even no more than 0.2 microliter.

This particular meter embodiment of FIG. 1 includes engagement detents 16. Detents 16 are configured to retain a port protector.

FIG. 2A shows an isometric front view of an exemplary embodiment of a port protector 30. Protector 30 includes a body 31. Within body 31 is formed slot 32. While the embodiment of FIG. 2A includes a slot, as noted above, certain embodiments do not include slots. In those embodiments that do not include a slot, the protector may be formed as a plug that cooperates with the port.

Protector 30 also includes tester positioning feature(s), in this embodiment in the form of guide grooves 33 positioned on opposing sides of the protector and a ledge or "diving board" feature 34.

Figure 2B:
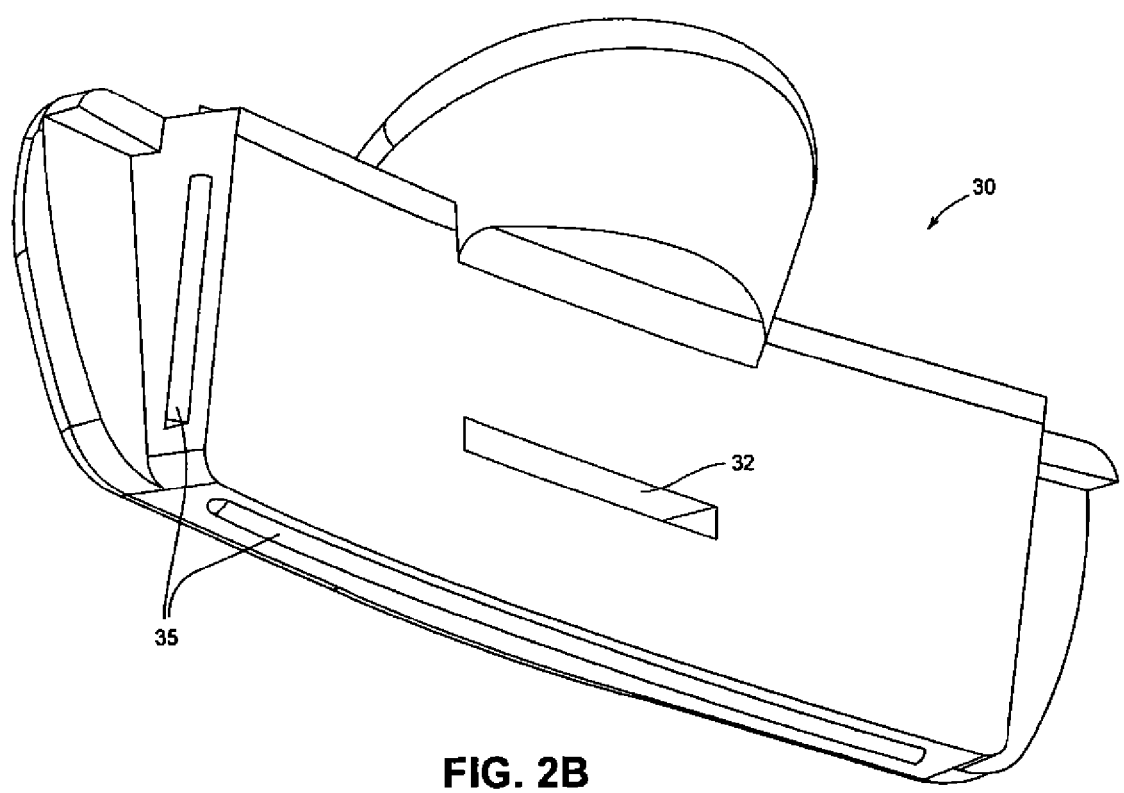
FIGS. 2B and 2C are isometric rear views of the protector of FIG. 2A.
Figure 2C:
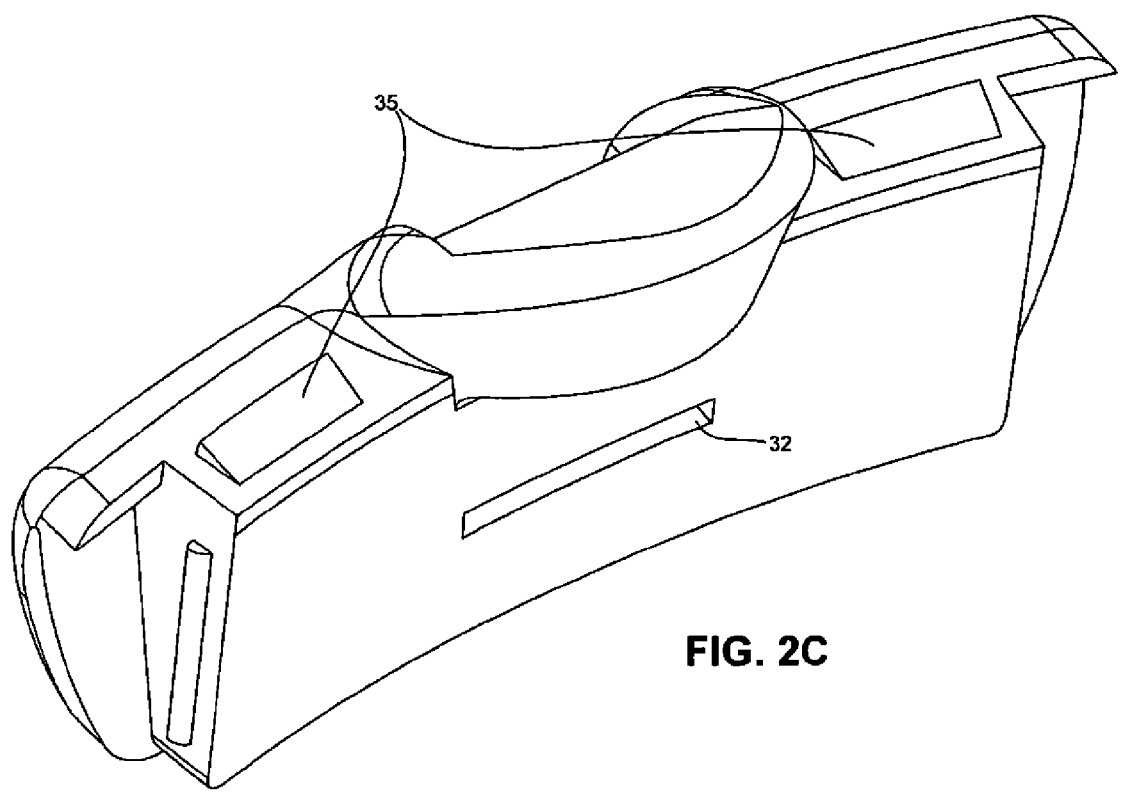

Protector 30 also includes attachment features. FIGS. 2B and 2C show isometric rear views of protector 30 showing engagement ribs 35. Attachment features 35 in this embodiment are in the form of engagement protrusions that extend outwardly from the protector. In certain embodiments the form of engagement may be indentations extending inwardly into the protector. Attachment features also serve to align the protector with the meter.

Engagement ribs 35 mate with detents on a meter, to hold the protector in place on the meter. Some or all of the back surface of protector 35 shown in FIGS. 2B and 2C may include adhesive thereon. Adhesive may be in addition to or in place of engagement ribs 35.

Figure 3:
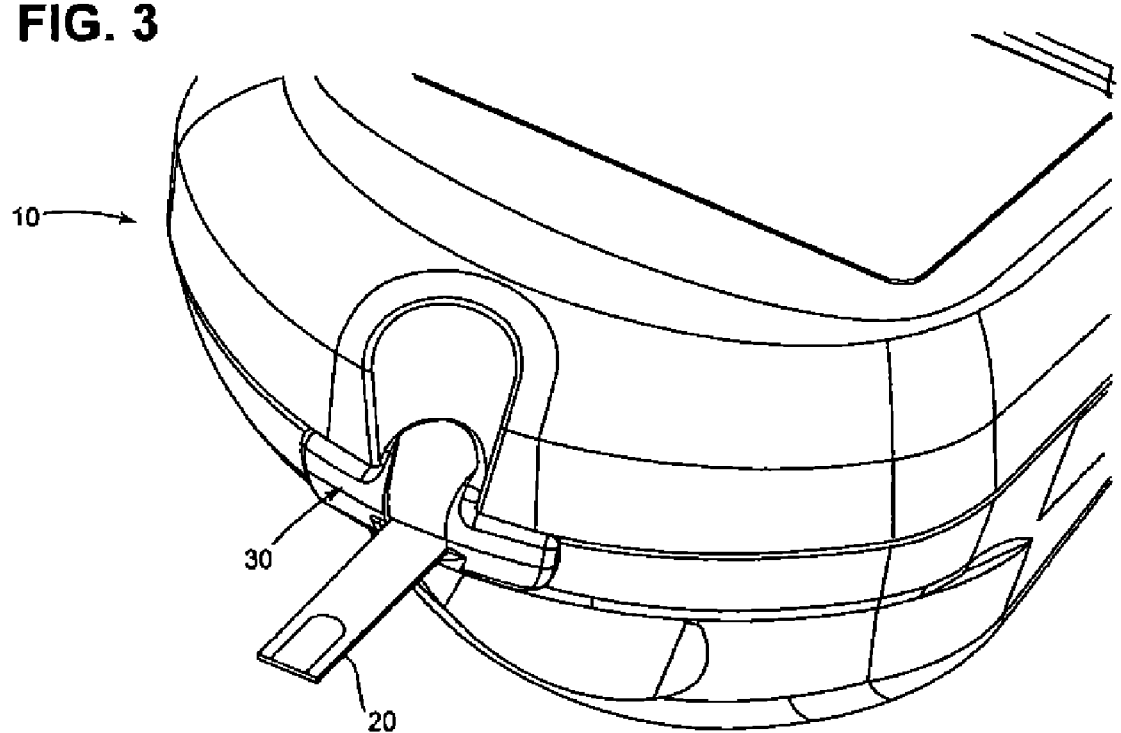
FIG. 3 is an isometric front view of the meter of FIG. 1 with the protector of FIGS. 2A-2C installed thereon.

FIG. 3 shows an isometric front view of meter 10 with protector 30 installed thereon. As shown, the protector narrows the opening to the interior of the meter.

To perform an analyte test, a sample of biological fluid is provided to the tester for analyte testing, where the level of analyte is determined. Sample may be applied to the tester before or after the tester is positioned in the meter. In many embodiments, it is the level of glucose in blood, interstitial fluid, and the like, that is determined. Also in many embodiments, the source of the biological fluid is a drop of blood drawn from a patient, e.g., after piercing the patient's skin with a lancing device or the like.

The invention has been described with reference to various specific and preferred embodiments and techniques. However, it will be apparent to one of ordinary skill in the art that many variations and modifications may be made while remaining within the spirit and scope of the invention.

All patents and other references in this specification are indicative of the level of ordinary skill in the art to which this invention pertains. All patents and patent applications are herein incorporated by reference to the same extent as if each individual patent was specifically and individually incorporated by reference.

We claim:

1. An electrochemical analyte meter, comprising:
 a housing defining an interior space in communication with the outside environment through an opening in the housing;
 a component removably attached to the housing about the housing opening, wherein the component includes a slot dimensioned to swipe across a surface of an in vitro analyte test strip when the test strip is received through the slot of the component, and wherein the component further includes an engagement feature that serves to align and attach the component to the housing.

2. The meter of claim 1, wherein the component provides a substantially fluid tight seal with the housing.

3. The meter of claim 1, wherein the component comprises an elastomeric material.

4. The meter of claim 3, wherein the component comprises rubber.

5. The meter of claim 3, wherein the component comprises adhesive.

6. The meter of claim 1, wherein the slot of the component comprises a test strip guide.

7. The meter of claim 6, wherein the guide comprises a ledge.

8. The meter of claim 1, wherein the meter is configured to be used with an in vitro analyte test strip that is configured to test for analyte in a sample of no more than about 1 microliter.

9. The meter of claim 8, wherein the analyte test strip is configured to test for analyte in a sample of no more than about 0.5 microliter.

10. The meter of claim 8, wherein the analyte test strip is configured to test for analyte in a sample of no more than about 0.2 microliter.

11. The meter of claim 1, wherein the meter is a glucose meter.

12. The meter of claim 1, wherein the meter is a ketone meter.

13. The meter of claim 1, wherein the component reduces the size of the opening of the housing when attached to the housing.

14. The meter of claim 1, wherein the meter is integrated with an in vivo analyte monitoring device.

15. The meter of claim 14, wherein the in vivo analyte monitoring device is a transmitter module.

16. The meter of claim 14, wherein the in vivo analyte monitoring device is a receiver module.

17. The meter of claim 1, wherein the slot is dimensioned to prevent contaminants from entering the interior space of the housing.

* * * * *